(12) United States Patent
Kang (10) Patent No.: US 10,435,436 B2
(45) Date of Patent: *Oct. 8, 2019

(54) COMPOSITION FOR IMPROVING MEMORY, LEARNING ABILITY, AND COGNITIVE ABILITY

(71) Applicant: Brainon Inc., Seoul (KR)

(72) Inventor: Yong Koo Kang, Seoul (KR)

(73) Assignee: BRAINON INC., Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/011,637

(22) Filed: Jun. 19, 2018

(65) Prior Publication Data

US 2018/0327451 A1 Nov. 15, 2018

Related U.S. Application Data

(62) Division of application No. 15/482,752, filed as application No. PCT/KR2016/004650 on May 3, 2016, now abandoned.

(30) Foreign Application Priority Data

Dec. 21, 2015 (KR) .................. 10-2015-0183011
Mar. 4, 2016 (KR) .................. 10-2016-0026600

(51) Int. Cl.
A61K 38/04 (2006.01)
C07K 7/06 (2006.01)
(Continued)

(52) U.S. Cl.
CPC ............ *C07K 5/1008* (2013.01); *A61K 38/08* (2013.01); *A61P 25/28* (2018.01); *C07K 5/10* (2013.01);
(Continued)

(58) Field of Classification Search
None
See application file for complete search history.

(56) References Cited

U.S. PATENT DOCUMENTS 5,243,038 A 9/1993 Ferrari et al.
6,069,129 A 5/2000 Sandberg et al.
(Continued)

FOREIGN PATENT DOCUMENTS

JP 10014586 A 1/1998
JP 2004511429 A 4/2004
(Continued)

OTHER PUBLICATIONS

Jun. 20, 2016, Korean Office Action for related KR application No. 10-2015-0183011.
(Continued)

*Primary Examiner* — Aurora M Fontainhas
(74) *Attorney, Agent, or Firm* — Rothwell, Figg, Ernst & Manbeck, P.C.

(57) ABSTRACT

There is provided a composition for improving memory, learning ability, and cognitive ability. It has been confirmed that a peptide having a C-terminal region ended to GAG had an effect of improving the memory. In order for the peptide to have the effect, it has been confirmed that the peptide should be a peptide of which the length consists of at least 4 amino acids. Further, it has been confirmed that a peptide of which the length of the peptide having the C-terminal region ended to GAG consists of 5 to 9 amino acids has the same effect. As a result, the peptide of the present invention can be used as the composition for improving memory, learning ability, and cognitive ability.

8 Claims, 4 Drawing Sheets

Specification includes a Sequence Listing.

(51) Int. Cl.
  *C07K 5/103* (2006.01)
  *A61K 38/08* (2019.01)
  *C07K 5/10* (2006.01)
  *C12P 21/00* (2006.01)
  *C12N 15/63* (2006.01)
  *A61P 25/28* (2006.01)
  *C07K 5/113* (2006.01)

(52) U.S. Cl.
  CPC .............. *C07K 5/1021* (2013.01); *C07K 7/06* (2013.01); *C12N 15/63* (2013.01); *C12P 21/00* (2013.01)

(56) References Cited

U.S. PATENT DOCUMENTS

| | | | |
|---|---|---|---|
| 2003/0176355 A1 | 9/2003 | Cappello et al. | |
| 2003/0192077 A1 | 10/2003 | Yang | |
| 2004/0116339 A1 | 6/2004 | Villanueva et al. | |
| 2004/0234609 A1 | 11/2004 | Collier et al. | |
| 2005/0227922 A1 | 10/2005 | Moessler et al. | |
| 2010/0093641 A1 | 4/2010 | Kim et al. | |
| 2013/0330335 A1* | 12/2013 | Bremel | G16B 20/00 424/134.1 |

FOREIGN PATENT DOCUMENTS

| | | |
|---|---|---|
| KR | 10-2004-0073425 A | 8/2004 |
| KR | 10-2007-0000892 A | 1/2007 |
| KR | 10-2007-0038947 A | 4/2007 |
| KR | 10-2008-0034559 A | 4/2008 |
| KR | 10-2013-0111237 A | 10/2013 |
| KR | 10-1430387 B1 | 8/2014 |
| KR | 101430387 B1 | 8/2014 |
| WO | WO01/90389 A2 | 11/2001 |
| WO | WO01/90389 A3 | 11/2001 |
| WO | 2011/067624 A1 | 6/2011 |
| WO | 2011/150061 A1 | 12/2011 |
| WO | 2012/092718 A1 | 7/2012 |

OTHER PUBLICATIONS

Yong Koo Kang et al: "Memory-Enhancing Effects of Silk Fibroin-Derived Peptides in Scopolamine-Treated Mice", Journal of Microbiology and Biotechnology., vol. 23,No. 12,Dec. 28, 2013 (Dec. 28, 2013), pp. 1779-1784, XP055456475,KR ISSN: 1017-7825, DOI: 10.4010/jmb.1308.08059.
International Search Report issued for International Application No. PCT/KR2016/004650 dated Sep. 12, 2016, 22 pages.
European Search Report issued for European Application No. 16879083.0 dated Mar. 16, 2018, 8 pages.
Australian Office Action issued for Australian Application No. 2016376059 dated Mar. 29, 2018, 7 pages.
Japanese Office Action issued for Japanese Application No. 2017-546737 dated Aug. 27, 2018, 6 pages.
Kim, Eun-Do, et al., "Fibroin-Derived Peptides Stimulate Glucose Transport in Normal and Insulin-Resistant 3T3-L1 Adipocytes", Biological and Pharmaceutical Bulletin, 32(3), p. 427-433, 2009.
L.-L. Guo, et al., "A Novel Specific Small Molecule Peptide for Non-small Cell Lung Cancer Cell A549", Progress in Biochemistry and Biophysics, 34(10):1080-1085, Oct. 2007, with English translation Abstract.
Canadian Office Action issued for Canadian Application No. 2,965,840, dated Mar. 20, 2018, 4 pages.
T. C. Elleman, "Aminopeptidases of Pea", Biochemical Journal, (1974), 141(1) pp. 113-118.
Tran C. D., et al., "Near-Infrared Spectrophotometric Determination of Tri- and Tetrapeptides", Analytical Biochemistry, (2000), 286(1), pp. 67-74.
Joo-Hong Yeo, et al., "Cognitive Ability Enhancement Effects in Rats by B. mori Fibroin Enzymatic Hydrolysate", Korean J. Seric. Sci., (2004), 46(1), pp. 23-27, with English translation.
"Fibroin heavy chain precursor [Bombyx mori]", Reference Sequence: NP_001106733.1, retrieved from <https://www.ncbi.nlm.nih.gov/protein/NP_001106733.1> on Sep. 14, 2018, 3 pages.
Australian Office Action issued for Australian Application No. 2016376059 dated Nov. 1, 2018, 3 pages.
Office Action issued for Canadian Patent Application No. 2,965,840 dated Dec. 7, 2018, 4 pages.
Office Action issued for Russian Patent Application No. 2018120516/04(032345) dated Feb. 28, 2019, with English translation, 11 pages.
Wu, Lianming et al., "Chiral Analysis Using the Kinetic Method with Optimized Fixed Ligands: Applications to Some Antibiotics", Analytical Chemistry, 2003, 75 (3), pp. 678-684.
Brunn-Leube, I. V., & Schramm, G. "Kondensation von Peptidmethylestern verschiedener Kettenlänge" Chemische Berichte, 1956, 89(9), 2045-2055, with Machine English Translation.
Helmut Zahn, Eugen Schnabel, "DL-Seryl-Glycyl-DL-Alanyl-Glycyl-DL-Alanyl-Glycin", European Journal of Organic Chemistry, 1957, 604(1):62-75, with Machine English Translation.
PubChem CID:18479567, Create Date: Dec. 4, 2007, retrieved from https://pubchem.ncbi.nlm.nih.gov/compound/18479567 (8 pages).
Aonuma, S. et al., "Studies on heart. XXIII. Distribution of (1-14C) Acetamidino-antiarrhythmic Peptide (14C-AAP) in Mice", Chemical & Pharmaceutical Bulletin, 1983, 31(2), 612-619.
Klok, H.-A., et al., "Synthesis of a silk-inspired peptide-oligothiophene conjugate", Org. Biomol. Chem., 2004, 2(24), 3541-3544.
Robinson, A. B., et al., "Rates of Nonenzymic Deamidation of Glutaminyl and Asparaginyl Residues in Pentapeptides", Journal of the American Chemical Society, 1973, 95(24), 8156-8159.
Jones, J. A. and Liebler D. C., "Tandem MS Analysis of Model Peptide Adducts from Reactive Metabolites of the Hepatotoxin 1,1-Dichloroethylene", Chemical Research in Toxicology, 2000, 13(12), 1302-1312.

* cited by examiner

COMPOSITION FOR IMPROVING MEMORY, LEARNING ABILITY, AND COGNITIVE ABILITY

CROSS-REFERENCE TO RELATED APPLICATIONS

This application is a divisional application of the U.S. application Ser. No. 15/482,752, filed Apr. 8, 2017, which is a 35 U.S.C. 371 National Phase Entry Application of PCT/KR2016/004650 filed May 3, 2016, which claims the benefit of earlier filing date and right of Korean Patent Application Nos. 10-2015-0183011, filed on Dec. 21, 2015 and 10-2016-0026600, filed on Mar. 4, 2016, the disclosure of which are incorporated herein in their entirety by reference.

TECHNICAL FIELD

The present invention relates to a composition for improving memory, learning ability, and cognitive ability.

BACKGROUND

The brain has various functions, but the most important function is memory and cognition. If there are no cognitive and memory abilities in the human, it is difficult to perform everyday life and it becomes a problem for survival. The memory and cognition are associated with almost all functions of the brain and brain structures associated with the memory and cognition are various and closely connected to almost all brain parts.

The memory are classified into several steps and divided into a step of registering and encoding information, a storing step, and a step of accessing and withdrawing to a place of memory.

The encoding refers to an initial process in which information entered into the brain through sensory organs is learned and memorized. The information is first stored through the encoding, but in order for the stored information to be continuously retained and stored more firmly, a process after encoding is required and this process is called consolidation. If the consolidation of the memory is not achieved well, memory forgetting occurs rapidly and memory retention becomes difficult. The withdrawal means a process of consciously invoking the contents stored in the long-term memory. The withdrawal method includes recalling and recognition. The recalling is to invoke consciously the contents of the memory and the recognition is to invoke the contents while hints are applied. In most cases, the recalling is more difficult than the recognition. However, like patients with frontal lobe injury or subcortical vascular dementia, the recalling is difficult, but the recognition is achieved well, and in this case, the encoding and the storing of the memory are performed well, but there is failure of the withdrawal. If there is a memory storage failure, both the recalling and the recognition have the failure.

In addition, short-term memory is also referred to as working memory, which is a process of performing the next task by using the information after storing the information for a short period. The short-term memory means a temporary stay before the information entering the brain hardens to the long-term memory. A feature of the working memory is working memory that is usually erased after performing a predetermined task.

The long-term memory means learning a new task and memorizing the new task again after a predetermined time elapses. Memorizing things which have been experienced in our daily lives or the contents which have been learned again after the time elapses corresponds to almost the long-term memory.

The memory and cognitive disorders correspond to very serious diseases that make daily life impossible, and includes diseases caused by a wide variety of causes and mechanisms, such as aging, Alzheimer's disease, schizophrenia, Parkinson's disease, Huntington's disease, pick disease, Creutzfeldt-Jakob disease, depression, aging, head injury, stroke, CNS hypoxia, cerebral ischemia, encephalitis, forgetfulness, traumatic brain injury, hypoglycemia, Wernicke-Korsakoff syndrome, drug addiction, epilepsy, fasciola hepatica, hippocampal sclerosis, headache, brain aging, dementia, frontotemporal lobar degeneration, tumor, normal pressure hydrocephalus, HIV, cerebrovascular disease, cerebral disease, cardiovascular disease, amnesia, radiation exposure, metabolic disease, hypothyroidism, mild cognitive impairment, cognitive deficiency and attention deficit. In order to solve the memory and cognitive disorders, the related art has made various efforts, but up to now, there have been no reports and application on the efficacy of synthetic peptides having precise sequences as well as substances having an excellent neuroprotective effect and a brain function improving effect against various brain-nervous system diseases.

SUMMARY

The present invention has been made in an effort to provide a peptide for improving memory, learning ability, and cognitive ability.

In order to achieve the above object, an exemplary embodiment of the present invention provides a peptide including an amino acid sequence with a C-terminal region of GAG.

In an exemplary embodiment of the present invention, preferably, the peptide is derived from a silk fibroin hydrolyzate, but is not limited thereto.

In another exemplary embodiment of the present invention, preferably, the peptide is artificially synthesized, but may not be limited thereto.

In yet another exemplary embodiment of the present invention, preferably, the peptide has the number of amino acid residues of 4 to 6, but is not limited to the length, and the peptide has an amino acid sequence of GGAG (SEQ ID NO:5), AGAG (SEQ ID NO:3), QGAG (SEQ ID NO:4), or SGAGAG (SEQ ID NO:6), but may not be limited to the amino acid sequence.

In still another exemplary embodiment of the present invention, preferably, the peptide has the number of amino acid residues of 5 to 9, and the peptide has an amino acid sequence of QAGAG (SEQ ID NO:7), SGGAG (SEQ ID NO:8), or GAGGAGGAG (SEQ ID NO:9), but may not be limited thereto.

The peptide of the present invention has excellent stability by itself, but in order to more largely improve the stability, various protection groups may be bound. Examples of the protection groups include an amino acid group, an acetyl group, a fluorenyl methoxycarbonyl group, a formyl group, a palmitoyl group, a myristyl group, a stearyl group and polyethylene glycol (PEG). The protection groups may be bound to various amino acid residues of the peptide of the present invention, but preferably may be bound to N- or C-terminals.

Furthermore, the present invention provides a pharmaceutical composition for preventing or treating a memory, cognitive, or learning disorder, including the peptide of the present invention as an active ingredient.

In an exemplary embodiment of the present invention, preferably, the memory, cognitive, or learning disorder is a memory, cognitive, or learning disorder caused by aging, Alzheimer's disease, schizophrenia, Parkinson's disease, Huntington's disease, pick disease, Creutzfeldt-Jakob disease, depression, aging, head injury, stroke, CNS hypoxia, cerebral ischemia, encephalitis, forgetfulness, traumatic brain injury, hypoglycaemia, Wernicke-Korsakoff syndrome, drug addiction, epilepsy, fasciola hepatica, hippocampal sclerosis, headache, brain aging, dementia, frontotemporal lobar degeneration, tumor, normal pressure hydrocephalus, HIV, cerebrovascular disease, cerebral disease, cardiovascular disease, amnesia, radiation exposure, metabolic disease, hypothyroidism, mild cognitive impairment, cognitive deficiency and attention deficit, but may not be limited thereto.

The composition may include a pharmaceutically acceptable carrier. The pharmaceutically acceptable carrier included in the composition is generally used in formulation, and includes lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, mineral oil, and the like, but may not be limited thereto. The pharmaceutical composition may further include lubricants, wetting agents, sweeteners, flavors, emulsifiers, suspensions, preservatives, and the like in addition to the ingredients.

The pharmaceutical composition may be administered orally or parenterally. In the case of the parenteral administration, intravenous injection, subcutaneous injection, muscle injection, intraperitoneal injection, endothelial administration, topical administration, intranasal administration, intrapulmonary administration, rectal administration, and the like may be performed.

During oral administration, since a protein or a peptide are digested, the oral composition may be formulated by coating an active agent or to be protected from decomposition in the stomach. Further, the composition may be administered by any apparatus in which an active substance may move to a target cell.

A suitable dose of the pharmaceutical composition may be variously prescribed by factors such as a formulation method, an administration type, age, weight, and gender of a patient, a pathological condition, food, an administration time, an administration route, an excretion rate, and a response susceptibility. A preferable dose of the composition may be in a range of 0.001 to 100 mg/kg based on an adult.

The term "pharmacologically effective dose" means a dose suitable for preventing or treating memory disorder, cognitive disorder or learning disorder.

The composition is formulated by using a pharmacologically acceptable carrier and/or excipient according to a method that may be easily performed by those skilled in the art to be prepared in a unit dosage form or prepared by intrusion into a multi-dose container. In this case, the formulation may be a form of solutions, suspensions, syrups or emulsions in oils or aqueous media or a form of extracts, discutient, powders, granules, tablets or capsules, and may additionally include a dispersant or a stabilizer. Further, the composition may be administered as an individual therapeutic agent or co-administered with other therapeutic agents, and sequentially or simultaneously administered with therapeutic agents in the related art.

Also, the present invention provides a food composition for enhancement of a brain or cognitive function, including the peptide of the present invention as an active ingredient.

In an exemplary embodiment of the present invention, preferably, the brain or cognitive function is a learning ability, a memory ability, or concentration, but may not be limited thereto.

An amount of the peptide in the food or drink of the present invention may be added with 0.01 to 15 wt % of the entire food weight, and a health drink composition may be added at a ratio of 0.02 to 5 g and preferably 0.3 to 1 g based on 100 ml, but it may be easily determined by those skilled in the art according to a product.

The food composition may further include a cytologically acceptable food supplementary additive in addition to the peptide and may be prepared in a form of tablets, capsules, pills, liquid preparations, jellies, powders, granules, and the like.

In the food composition of the present invention, other ingredients are not particularly limited except for including the peptide as the required ingredient, and like a general drink, various flavoring agents, natural starches, or the like may be included as an additional ingredient. Examples of the aforementioned natural carbohydrates include general sugars, such as monosaccharides, for example, glucose, fructose, and the like; disaccharides, for example, maltose, sucrose, and the like; and polysaccharides, for example, dextrin, cyclodextrin, and the like, and sugar alcohols, such as xylitol, sorbitol, and erythritol. As the flavoring agent other than the above examples, natural flavoring agents (thaumatin, stevia extract (for example, rebaudioside A, glycyrrhizin, and the like) and synthetic flavoring agents (saccharin, aspartame, and the like) may be advantageously used. A ratio of the natural carbohydrate may be generally about 1 to 20 g and preferably about 5 to 12 g per 100 ml of the composition of the present invention.

The food composition of the present invention may include various nutrients, vitamins, minerals (electrolytes), flavoring agents such as synthetic flavoring agents and natural flavoring agents, coloring agents and thickening agents (cheese, chocolate, and the like), pectic acid and salt thereof, alginic acid and salt thereof, organic acid, a protective colloidal thickener, a pH adjusting agent, a stabilizer, a preservative, glycerin, alcohol, a carbonic acid agent used in a carbonated drink, or the like, in addition to the ingredients. Besides, the food composition of the present invention may include pulps for preparing natural fruit juice and fruit juice drinks, and vegetable drinks. The ingredients may be used independently or in combination. The ratio of the additives is generally selected in a range of 0 to 20 parts by weight per 100 parts by weight of the compound of the present invention.

Further, the present invention provides a polynucleotide encoding the peptide of the present invention.

The "polynucleotide" is a polymer of a deoxyribonucleotide or a ribonucleotide which is present in a form of a single strand or a double strand. The polynucleotide includes an RNA genome sequence, DNA (gDNA and cDNA) and an RNA sequence transcribed therefrom, and includes analogs of natural polynucleotides unless specifically stated otherwise.

The polynucleotide includes not only the nucleotide sequence but also a complementary sequence to the nucleotide sequence. The complementary sequence includes not only a completely complementary sequence but also a substantially complementary sequence. The sequence means a sequence which may hybridize with the nucleotide sequence under stringent conditions which are known in the art.

Further, the polynucleotide may be modified. The modification includes addition, deletion, or non-conservative substitution or conservative substitution of the nucleotide. It is understood that the polynucleotide encoding the amino acid sequence includes a nucleotide sequence having substantial identity with respect to the nucleotide sequence. The substantial identity may be a sequence having homology of at least 80%, homology of at least 90%, or homology of at least 95%, in the case of analyzing a sequence which is aligned to maximally correspond to any different sequence from the nucleotide sequence and aligned by using a generally used algorithm in the art.

Furthermore, the present invention provides a recombinant vector including the polynucleotide of the present invention.

The term "vector" means a means for expressing a target gene in a host cell. For example, the vector includes a plasmid vector, a cosmide vector, and virus vectors such as a bacteriophage vector, an adenovirus vector, a retrovirus vector, and an adeno-associated virus vector. The vector which may be used as the recombinant vector may be prepared by manipulating plasmids (for example, pSClOl, pGV1106, pACYC177, ColE1, pKT230, pME290, pBR322, pUC8/9, pUC6, pBD9, pHC79, pIJ61, pLAFR1, pHV14, pGEX series, pET series, pUC19, and the like), phages (for example, Agt4AB, A-Charon, A zl, M13, and the like) or virus (for example, CMV, SV40, and the like).

In the recombinant vector, the polynucleotide encoding the peptide may be operatively linked with a promoter.

The term "operatively linked" means a functional binding between a nucleotide expression regulatory sequence (for example, a promoter sequence) and a different nucleotide sequence. Accordingly, the regulatory sequence may regulate transcription and/or translation of the different nucleotide sequence by the functional binding.

The recombinant vector may be typically constructed as a vector for cloning or a vector for expression. The expression vector may use general vectors which are used to express foreign proteins in plants, animals, or microorganisms in the art. The recombinant vector may be constructed by various methods known in the art.

The recombinant vector may be constructed by using a prokaryotic cell or an eukaryotic cell as a host. For example, the used vector is an expression vector, and in the case of using the prokaryotic cell as a host, the vector generally includes a strong promoter (for example, a pLA promoter, a trp promoter, a lac promoter, a tac promoter, a T7 promoter, and the like), a ribosome binding site for initiation of translation, and a transcription/translation termination sequence. In the case of using the eukaryotic cell as a host, a replication origin that functions in the eukaryotic cell included in the vector includes an fl replication origin, an SV40 replication origin, a pMB1 replication origin, an adeno replication origin, an AAV replication origin, a CMV replication origin, a BBV replication origin, and the like, but is not limited thereto. Further, a promoter (for example, a metallothionein promoter) derived from a genome of a mammalian cell or a promoter (for example, a adenovirus late-phase promoter, a vaccinia virus 7.SK promoter, an SV40 promoter, a cytomegalovirus (CMV) promoter and a tk promoter of HSV) derived from a mammalian virus may be used, and a polyadenylation sequence is generally used as a transcription termination sequence.

Also, the present invention provides a host cell transformed with the recombinant vector of the present invention.

The host cell of the present invention may use any host cell known in the art, and as the prokaryotic cell, for example, *E. coli* strains, such as *E. coli* JM109, *E. coli* BL21, *E. coli* RR1, *E. coli* LE392, *E. coli* B, *E. coli* X 1776, and *E. coli* W3110, *Bacillus subtilis* strains, such as *Bacillus subtilis* and *Bacillus thuringiensis*, and enterobacteriaceae and strains, such as *Salmonella typhimurium, Serratia marcesensis* and various *Pseudomonas* species are included. In the case of transformation to the eukaryotic cell, as the host cell, yeast (*Saccharomyce cerevisiae*), insect cells, plant cells and animal cells, for example, SP2/0, CHO (Chinese hamster ovary) K1, CHO DG44, PER.C6, W138, BHK, COS-7, 293, HepG2, Huh7, 3T3, RIN, MDCK cell lines, and the like may be used.

Further, the present invention provides a method for preparing the peptide of the present invention including incubating the host cell of the present invention.

The insertion into the host cell of the polynucleotide or the recombinant vector including the polynucleotide may use an insertion method which is well-known in the art. The transfer method may use a CaCh method or an electroporation method, or the like when the host cell is the prokaryotic cell, and use microinjection, calcium phosphate precipitation, electroporation, liposome-mediated transfection and gene bombardment when the host cell is the eukaryotic cell, but is not limited thereto.

A method of screening the transformed host cell may be easily performed by using a phenotype expressed by a selection marker according to a method well-known in the art. For example, when the selection marker is a specific antibiotic resistance gene, a transformant may be easily screened by incubating the transformant in a medium including the antibiotic.

According to the present invention, it has been confirmed that a peptide having a C-terminal region ended to GAG had an effect of improving the memory. In order for the peptide to have the effect, it has been confirmed that the peptide should be a peptide of which the length consists of at least 4 amino acids. Further, it has been confirmed that a peptide of which the length of the peptide having the C-terminal region ended to GAG consists of 5 to 9 amino acids has the same effect. As a result, the peptide of the present invention can be used as a composition for improving memory, learning ability, and cognitive ability.

DETAILED DESCRIPTION OF THE INVENTION

Hereinafter, the present invention will be described in more detail through Examples. However, these Examples are to exemplify the present invention and the scope of the present invention is not limited to these Examples.

Example 1: Synthesis of Peptides

Synthesized peptides were obtained from Genscript (New Jersey, USA). The peptides were synthesized by a flexpeptide technology method and confirmed by using high pressure liquid chromatography and mass spectrometry. Amino acid sequences of the synthesized peptides are as listed in Table 1.

TABLE 1

| Peptide name (sequence number) | Amino acid sequence | |
|---|---|---|
| Peptide-1 | AG | (SEQ ID NO: 1) |
| Peptide-2 | GAG | (SEQ ID NO: 2) |
| Peptide-3 | AGAG | (SEQ ID NO: 3) |
| Peptide-4 | QGAG | (SEQ ID NO: 4) |
| Peptide-5 | GGAG | (SEQ ID NO: 5) |
| Peptide-6 | SGAGAG | (SEQ ID NO: 6) |

Further, the present inventors additionally synthesized peptides (sequence numbers 7 to 9) of amino acid sequences 5 to 9 to perform an additional test. These synthesized peptides were obtained from Genscript (New Jersey, USA). The peptides were synthesized by a flexpeptide technology method and confirmed by using high pressure liquid chromatography and mass spectrometry. The amino acid sequences of the synthesized peptides are as follows;

QAGAG (SEQ ID NO: 7)

SGGAG (SEQ ID NO: 8)

GAGGAGGAG (SEQ ID NO: 9)

Example 2: Reagents and Animals

Scopolamine was purchased from Sigma-Aldrich (St. Louis, Mo., USA). 4-week-old male ICR mice were purchased from Korean BioLink Co. (Chungbuk, Korea). After an adaptation period of one week, the mice were used in a test and all reagents were administered intraperitoneally. Memory disorder was induced by injection of scopolamine before 30 minutes of the test and the synthesized peptides were injected before 30 minutes of the injection of scopolamine.

Example 3: Confirmation of Effect of Peptides in Passive Avoidance Test

A passive avoidance test was performed in the same bright room and dark room. A floor of each room was formed in a shape in which 2-mm stainless steel rods were separated from each other at 1-cm intervals. Bright squares (20×20×20 cm) had 100-W bulbs. These squares were connected to a guillotine door.

For an acquisition trial, the mouse was placed in the bright room after injection of the reagents and the door was opened after 10 seconds. When the mouse completely entered the dark room, the door was closed and electric shock was applied for 3 seconds. A retention trial was performed after 24 hours of the acquisition trial and the mouse was positioned in the bright room. A latency time of the acquisition and retention trials was measured by a time until the mouse entered the dark room of the box after the door was opened.

The retention latency in the passive avoidance test represents a long-term memory function in rodents. Accordingly, an effect of a silk fibroin peptide on scopolamine-induced memory deterioration was confirmed by using a step-through passive avoidance test and the result was illustrated in FIG. 1.

Figure 1:
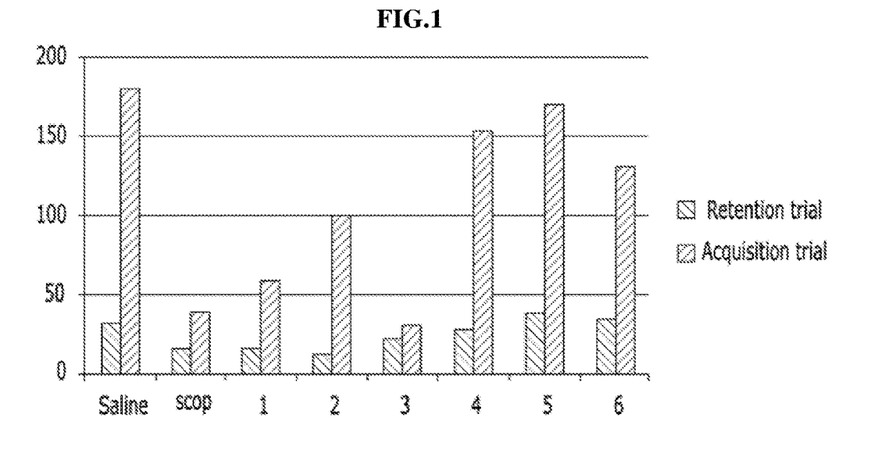
FIG. 1 is a diagram illustrating a memory enhancing effect of a peptide of which an amino acid sequence of a C-terminal region is GAG through a passive avoidance test. A y axis is time (sec).

As illustrated in FIG. 1, in the retention trial, a latency time of a normal saline-treated mouse was 180 seconds (maximum cut-off time). It was confirmed that an average of the step-through responses in a scopolamine-injected group with memory deterioration due to injection of scopolamine was significantly lowered as compared with a normal saline-treated group. Before administration of scopolamine, in groups administered with the synthesized peptides, in a peptide-I-administered group consisting of two amino acids, slight improvement was achieved compared with the scopolamine-administered group, and in a peptide-3-administered group, there was a little effect as compared with the scopolamine-administered group. However, it was confirmed that in peptide-2 and peptide-4 to 6-administered groups, the deteriorated memory by scopolamine was improved to be close to a normal group administered with saline. From the above result, it was confirmed that there was a memory improving effect of the peptide of which the C-terminal region ended to GAG, and in order to have the effect, it is confirmed that the peptide should be a peptide in which the length consists of at least four amino acids.

Figure 3:
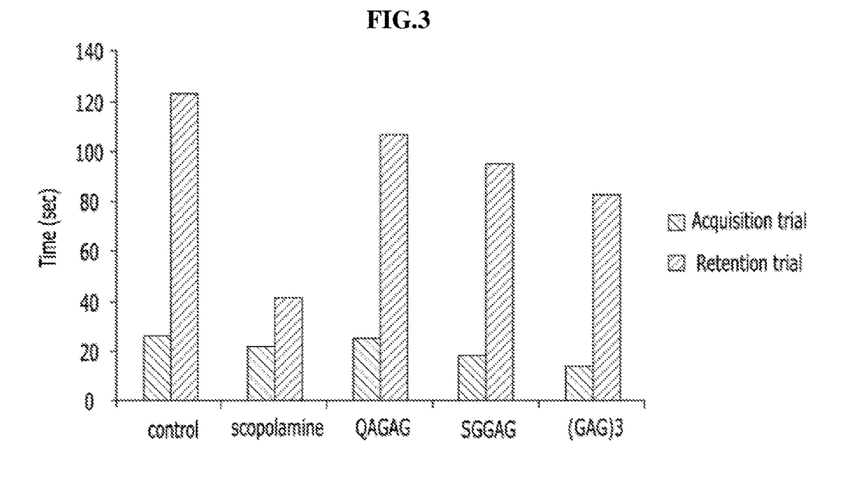
FIG. 3 is a diagram illustrating a memory enhancing effect of a peptide of which an amino acid sequence of a C-terminal region consisting of 5 to 9 amino acids is GAG through a passive avoidance test, including QAGAG (SEQ ID NO:7) and SGGAG (SEQ ID NO:8).

As illustrated in FIG. 3, in the retention trial, a latency time of a normal saline-treated mouse was 180 seconds (maximum cut-off time). It was confirmed that an average of the step-through responses in a scopolamine-injected group with memory deterioration due to injection of scopolamine was significantly lowered as compared with a normal saline-treated group. Before administration of scopolamine, it was confirmed that in a group administered with the peptide consisting of 5 to 9 amino acids of the present invention, the memory deteriorated by scopolamine was improved to be close to the normal group administered with saline. From the above result, the memory improving effect of the peptide of which the C terminal region ended to GAG was confirmed.

Example 4: Confirmation of Effect of Peptide in Y Maze Test

The mouse was placed at one end of a Y maze with a length of one branch of 30 cm, a width of 5 cm, and a height of 13 cm and the order of entry into each branch was recorded. Alternation was judged to be successful if the mouse sequentially entered three different branches. Spontaneous alternation was defined as Equation below.

Spontaneous alternation (%)=the number of alternations/(total number of entries−2)×100

Figure 2:
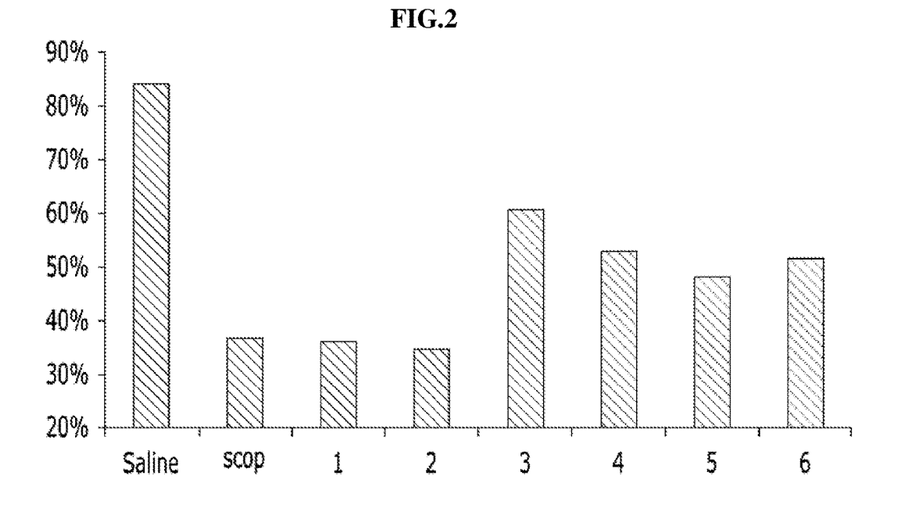
FIG. 2 is a diagram illustrating a memory enhancing effect of a peptide of which an amino acid sequence of a C-terminal region is GAG through a Y maze test. A y axis is spontaneous alternation (%).

As illustrated in FIG. 2, it was confirmed that the mean of spontaneous alternations of a scopolamine-injected group with memory deterioration due to the injection of scopolamine was significantly lower than that of the normal saline group. In groups administered with the synthesized peptides before administration of scopolamine, it was confirmed that in a peptide-I and 2 administered group consisting of 2 and 3 amino acids, slight improvement was achieved as compared with the scopolamine-administered group, but in a peptide-3 to 6 administered group consisting of the number of amino acids of 4 to 6, the memory deteriorated by scopolamine was significantly improved. From the above result, it was confirmed that there was a memory improving effect of the peptide of which the C-terminal region ended to GAG, and in order to have the effect, it is confirmed that the peptide should be a peptide in which the length consists of at least four amino acids.

Figure 4:
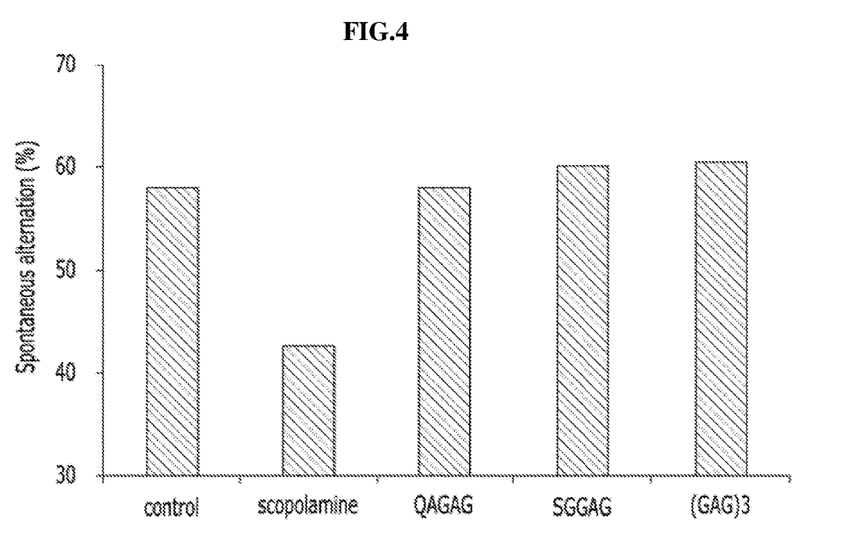
FIG. 4 is a diagram illustrating a memory enhancing effect of a peptide of which an amino acid sequence of a C-terminal region consisting of 5 to 9 amino acids is GAG through a Y maze test, including QAGAG (SEQ ID NO:7) and SGGAG (SEQ ID NO:8).

Further, as illustrated in FIG. 4, it was confirmed that the mean of spontaneous alternations of a scopolamine-injected group with memory deterioration due to the injection of scopolamine was significantly lowered as compared with the normal saline group. In the group administered with the peptide consisting of 5 to 9 amino acids of the present invention before administration of scopolamine, the memory deteriorated by scopolamine was significantly improved, and in the group administered with peptides of sequence numbers 2 and 3, there was an excellent effect as compared with a control group. From the above result, the memory improving effect of the peptide of which the C terminal region ended to GAG was confirmed.

What is claimed is:

1. A peptide which consists of SEQ ID NO: 9 (GAG-GAGGAG) that is bound to one or more protection groups and wherein the one or more protection groups are selected from an acetyl group, a fluorenyl methoxycarbonyl group, a formyl group, a palmitoyl group, a myristyl group, a stearyl group or polyethylene glycol.

2. The peptide of claim 1, wherein the peptide is artificially synthesized.

3. A pharmaceutical composition for treating a memory, cognitive, or learning disorder, comprising the peptide of claim 1 as an active ingredient.

4. The pharmaceutical composition of claim 3, wherein the memory, cognitive, or learning disorder is a memory, cognitive, or learning disorder caused by aging, Alzheimer's disease, schizophrenia, Parkinson's disease, Huntington's disease, pick disease, Creutzfeldt-Jakob disease, depression, aging, head injury, stroke, CNS hypoxia, cerebral ischemia, encephalitis, forgetfulness, traumatic brain injury, hypoglycaemia, Wernicke-Korsakoff syndrome, drug addiction, epilepsy, fasciola hepatica, hippocampal sclerosis, headache, brain aging, dementia, frontotemporal lobar degeneration, tumor, normal pressure hydrocephalus, HIV, cerebrovascular disease, cerebral disease, cardiovascular disease, amnesia, radiation exposure, metabolic disease, hypothyroidism, mild cognitive impairment, cognitive deficiency, or attention deficit.

5. The pharmaceutical composition of claim 3, further comprising a pharmaceutically acceptable carrier selected from the group consisting of lactose, dextrose, sucrose, sorbitol, mannitol, starch, acacia rubber, calcium phosphate, alginate, gelatin, calcium silicate, microcrystalline cellulose, polyvinylpyrrolidone, cellulose, syrup, methylcellulose, methylhydroxybenzoate, propylhydroxybenzoate, talc, magnesium stearate, mineral oil, or a combination thereof.

6. A food composition for enhancement of a brain or cognitive function, the food composition comprising the peptide of claim 1 as an active ingredient.

7. The food composition of claim 6, wherein the brain or cognitive function is a learning ability, a memory ability, or concentration.

8. The food composition of claim 6, further comprising a cytologically acceptable additive selected from the group consisting of flavoring agents, starches, carbohydrates, nutrients, vitamins, minerals, electrolytes, coloring agents, thickening agents, pectic acid or salt thereof, alginic acid or a salt thereof, an organic acid, pH adjusting agents, stabilizers, preservatives, glycerin, alcohol, carbonic acid agents, or a combination thereof.

* * * * *

```
                        SEQUENCE LISTING

<160> NUMBER OF SEQ ID NOS: 9

<210> SEQ ID NO 1
    <211> LENGTH: 2
    <212> TYPE: PRT
    <213> ORGANISM: Artificial Sequence
    <220> FEATURE:
    <223> OTHER INFORMATION: peptide

<400> SEQUENCE: 1

Ala Gly
    1

<210> SEQ ID NO 2
    <211> LENGTH: 3
    <212> TYPE: PRT
    <213> ORGANISM: Artificial Sequence
    <220> FEATURE:
    <223> OTHER INFORMATION: peptide

<400> SEQUENCE: 2

Gly Ala Gly
    1

<210> SEQ ID NO 3
    <211> LENGTH: 4
    <212> TYPE: PRT
    <213> ORGANISM: Artificial Sequence
    <220> FEATURE:
    <223> OTHER INFORMATION: peptide

<400> SEQUENCE: 3

Ala Gly Ala Gly
    1

<210> SEQ ID NO 4
    <211> LENGTH: 4
    <212> TYPE: PRT
    <213> ORGANISM: Artificial Sequence
    <220> FEATURE:
    <223> OTHER INFORMATION: peptide

<400> SEQUENCE: 4

Gln Gly Ala Gly
    1

<210> SEQ ID NO 5
    <211> LENGTH: 4
    <212> TYPE: PRT
    <213> ORGANISM: Artificial Sequence
    <220> FEATURE:
```

```
<223> OTHER INFORMATION: peptide

<400> SEQUENCE: 5

Gly Gly Ala Gly
1

<210> SEQ ID NO 6
<211> LENGTH: 6
<212> TYPE: PRT
<213> ORGANISM: Artificial Sequence
<220> FEATURE:
<223> OTHER INFORMATION: peptide

<400> SEQUENCE: 6

Ser Gly Ala Gly Ala Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Mutant

<400> SEQUENCE: 7

Gln Ala Gly Ala Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Mutant

<400> SEQUENCE: 8

Ser Gly Gly Ala Gly
1               5

<210> SEQ ID NO 9
<211> LENGTH: 9
<212> TYPE: PRT
<213> ORGANISM: Artificial Sequence
<220> FEATURE:
<223> OTHER INFORMATION: Mutant

<400> SEQUENCE: 9

Gly Ala Gly Gly Ala Gly Gly Ala Gly
1               5
```